United States Patent [19]

Tabatabi et al.

[11] Patent Number: 5,188,936

[45] Date of Patent: Feb. 23, 1993

[54] BRUCELLA ABORTUS ANTIBODY DETECTION METHODS

[75] Inventors: Louisa B. Tabatabi; John E. Mayfield, both of Ames, Iowa; Bonnie L. Beck, Waterbury, Conn.

[73] Assignee: The United States of America as represented by the Secretary of Agriculture, Washington, D.C.

[21] Appl. No.: 641,346

[22] Filed: Jan. 16, 1991

[51] Int. Cl.$^5$ .................... G01N 33/569; C12N 15/53
[52] U.S. Cl. .................................. 435/7.32; 435/7.4; 435/174; 435/189
[58] Field of Search ...................... 435/7.32, 7.4, 174, 435/176, 177, 180, 243, 189; 424/87, 92; 530/300, 327, 350, 389.1, 389.5

[56] References Cited

PUBLICATIONS

Tabatabai et al. "Specific Enzyme-Linked Immunosorbent Assay for Detection of Bovine Antibody to Brucella abortus", J. Clin. Microbiol. 20(2): 209–213 (Aug. 1984).

Hopp et al, "Prediction of protein antigenic determinants from amino acid sequences" Proc. Natl. Acad. Sci. USA 78(6): 3824–3828 (Jun. 1981).

Louisa B. Tabatabai et al., "Immunogenicity of Brucella abortus Salt-Extractable Proteins," Vet. Microbiol. 20: 49–58 (1989).

Bonnie L. Beck et al., "A Protein Isolated from Brucella abortus is a Cu-Zn Superoxide Dismutase," Biochemistry 29: 374–376 (1990).

Betsy J. Bricker et al., "Cloning, Expression, and Occurrence of the Brucella Cu-Zn Superoxide Dismutase," Infect. Immun. 58(9): 2935–2939 (Sep. 1990).

L. B. Tabatabai et al., "Characterization of Salt-Extractable Protein Antigens from Brucella abortus . . . " Vet. Microbiol. 9: 549–560 (1984).

M. Thompson et al., "Comparison of Brucella abortus Protein-Enzyme-Immunoassays and Conventional Serologic Tests for Detecting Bovine Antibody to B. abortus, "Abstr. #84, Iowa Academy of Science, Apr. 20-21, 1990.

Louisa B. Tabatabai et al., "Isolation and Characterization of Toxic Fractions from Brucella abortus," Infect. Immun. 26(2): 668–679 (Nov. 1979).

Primary Examiner—Esther L. Kipplinger
Assistant Examiner—Carol E. Bidwell
Attorney, Agent, or Firm—M. Howard Silverstein; John D. Fado; Curtis P. Ribando

[57] ABSTRACT

Diagnostic reagents comprising the 20 kd Brucella abortus CuZn superoxide dismutase (B. abortus lCuZnSOD) protein and peptide segments thereof, which are effective as antigenic determinants, have been identified. These reagents are useful for detecting an antibody response to the *B. abortus* CuZnSOD protein in bovine serum or other body fluid samples and can also be used for distinguishing between animals which have serum antibody of a natural *B. abortus* infection and those which have an antibody response to a *B. abortus* Strain 19 vaccine or a *B. abortus* Strain which does not express the 20 kd protein.

7 Claims, 4 Drawing Sheets

```
  1                          10                        20                        30                        40                       50
  ESTTVKMYEALPTGPGKEVGTVVISEAPGGLHFKVNMEKLTPGYHGFHVH
   └─CB1─┘       └────CB2────┘  └─────────────CB3─────────────
                         └─────────N-TERMINAL─────────┘
                              └────────CL1────────┘

60                        70                        80                        90                      100
  ENPSCAPGEKDGKIVPALAAGGHYDPGNTHHHLGPEGDGHMGDLPRLSAN
  ──────────────────────────┘   └────────CB4────────┘
                                         └─CL2─┘

110                       120                       130                       140                     150
  ADGKVSETVVAPHLKKLAEIKQRSLMVHVIGGDNVSDKPLPLGGGGARFAC
                         └──────────────┘ └──────CB5──────┘
         └──────SA10──────┘    └────CL3────┘ └──SA11──┘
                                                    └─CL4─┘

┌────┐
  │GVIE│┐┐┐┐
  └────┘
```

BRUCELLA ABORTUS ANTIBODY DETECTION METHODS

BACKGROUND OF THE INVENTION

1. Field of the Invention

This invention relates to a protein of *Brucella abortus* and to a specific region thereof useful as diagnostic reagents.

2. Description of the Prior Art

Bovine brucellosis is a disease associated with abortions and infertility, and is caused by the gram-negative organism *B. abortus*. Despite an active vaccination program, bovine brucellosis continues to be a problem in some areas in the United States ([*Hagen and Bruners' Infectious Diseases of Domestic Animals*. Ithaca, NY, Gillespie, J. H., et al., eds., 7th Edition, Cornell University Press; Manthei, C. A., et al., *The Yearbook of Agriculture. Proc. Anim. Dis.* 84th Congr., Second Session, House Document No. 344, U.S. Department of Agriculture, 1956] and is an economically important disease. Standard serologic tests for bovine brucellosis have been in use since 1940 [Manthei et al., supra], but the most difficult task has been in distinguishing antibodies of infected from those of vaccinated animals. To date, most diagnostic tests for *B. abortus* rely on detecting a humoral immune response, although the most definitive diagnostic test is bacterial culture and positive identification of *B. abortus* [Alton, G. G., et al., *Laboratory Techniques in Brucellosis*. Washington, D.C., Second edition, World Health Organization, 1975]. The bovine anti-Brucella antibody response is not only directed to the lipopolysaccharide (LPS) component of the cell [Lamb, V. L., et al., *Inf. Immun.* 26: 240–247 (1979); Ruppanner, R., et al., *Am. J. Vet. Res.* 41: 1329–1332 (1980); Saunders, G. C., et al., *J. Infect. Dis.* 136:5258–5266 (1977), but also to the proteins and other macromolecular components [Nielsen, K. H., et al., *Res. Vet. Sci.* 35: 14–18 (1983); Schurig, G. G., et al., Infect. Immun. 21: 994–1002 (1978); Stemshorn, B. W., et al., *Can. J. Comp. Med.* 41: 152–159 (1977); Tabatabai, L. B., et al., *Dev. Biol. Stand.* 56: 199–211 (1984); Tabatabai, L. B., et al., *Vet. Microbiol.* 9: 549–560 (1984); Tabatabai, L. B., et al., *J. Clin. Microbiol.* 20: 209–213]. However, serologic reactions following vaccination with *B. abortus* abortus Strain 19 interfere with diagnosis of brucellosis (using the card test) unless supplemental tests are performed, such as the rivanol and complement fixation tests [Alton, supra; Manthei, supra]. Recent progress in the development of procedures for diagnosis of brucellosis has been reviewed [Stemshorn, B. W., *Dev. Biol. Stand.* 56: 325–340 (1984)]. Specifically, a competitive enzyme-linked immunosorbent assay (ELISA) procedure based on O-chain and competing monoclonal antibodies has shown promising results [Nielsen, K. H., et al., *Ann. Inst. Pasteur, Microbiol.* 138: 69–144 (1987)]. It has been previously reported that *B. abortus* salt-extractable proteins (BCSP) could be used in a sensitive ELISA procedure for detecting brucellosis in cattle [Tabatabai, L. B., et al., *Vet. Microbiol.*, 9: 549–560 (1984)], and also for differentiating between vaccinated (calfhood vaccinated) and infected cattle using a Western blot procedure [Belzer, C. A., et al., *Vet. Microbiol.* 27: 12 pp. (in press, accepted for publication Sep. 20, 1990)]. However, approximately 3% of the animals that were vaccinated when sexually mature reacted also with the antigens [Belzer, supra]. We have shown that one of these proteins detects antibody to infected but not vaccinated cattle [Thompson, M., et al., Ann. Mtg. Iowa Acad. Sci., April 20–21, 1990, Drake University, Abstract No. 84]. Recently, we cloned the gene coding for this protein [Bricker, B. J., et al., *Inf. Immun.* 58: 2935–2939 (1990)] and have presented evidence that the recombinant protein also detects antibody to *B. abortus* of infected but not vaccinated animals [Thompson, supra].

Figure 1:
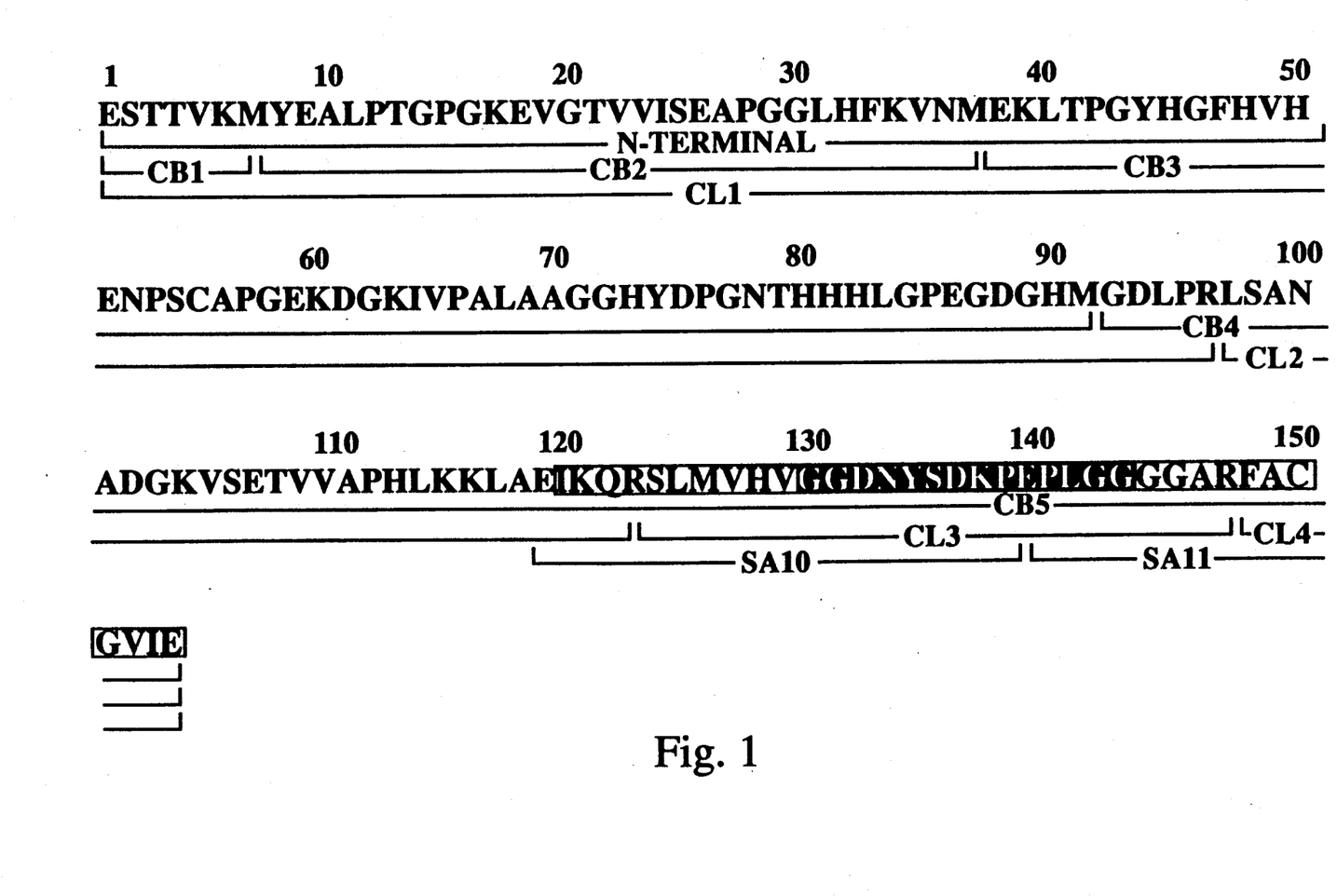

As described in Tabatabai et al. [Tabatabai, L. B., et al., *Infect. Immun.* 26: 668–679 (1979)], and as modified in Belzer et al. (supra) washed methanol-inactivated cells of *B. abortus* were resuspended in M NaCl-0.1M sodium citrate and stirred overnight. The protein mixture in the supernatant thus obtained was precipitated with ammonium sulfate to obtain the protein mixture. Polyacrylamide gel electrophoresis indicated the presence of a protein of approximate molecular weight of 20,000 daltons [Tabatabai et al., *Infect. Immun.*, supra, FIG. 4, page 674; and Tabatabai, L. B. et al., *Vet. Microbiol.* 20: 49–58 (1989), FIG. 1, page 55], but the procedure was not practical for use in preparing antiserum to the protein.

It has been suggested that the mixture of soluble salt-extractable proteins from *B. abortus* may be of potential value for preparing vaccines and/or for use as diagnostic reagents in the prevention or diagnosis of bovine brucellosis [Tabatabai et al., *Vet. Microbiol.* 9: 549–560 (1984), supra]. Further, the salt-extractable proteins of *B. abortus* have been analyzed by crossed immunoelectrophoresis using rabbit antiserum to protein antigens and by isoelectric focusing with polyacrylamide gels [Tabatabai et al., *Dev. Biol. Stand.*, and *Vet. Microbiol.*, supra]. The isoelectric pH's of the extracted proteins were profiled in FIG. 4, page 557, of Tabatabai et al., *Vet. Microbiol.*, supra.

SUMMARY OF THE INVENTION

We have now identified the 20 kd protein of *B abortus* as a Cu-Zn superoxide dismutase (SOD). We have succeeded in cloning the gene coding for the *B. abortus* Strain 19 CuZn superoxide dismutase (*B. abortus* CuZn-SOD), [Bricker et al., *Inf. Immun.* 58: 2935–2939 (1990)]. We have also succeeded in applying the amino acid sequence information of Beck et al. [*Biochem.* 29: 372–376 (1989)] for the 20 kd *B. abortus* CuZnSOD protein to the identification of regions corresponding to the antigenic determinants, or epitopes. The *B. abortus* CuZnSOD protein as well as peptides encompassing the antigenic determinant region are useful for detecting an antibody response to the *B. abortus* CuZnSOD protein.

If cattle have been vaccinated with the vaccine strain of *B. abortus* or vaccinated with a mutant strain of *B. abortus* which does not express the CuZnSOD protein, the diagnostic reagents of the invention are also useful for distinguishing between animals which had a natural infection and those which have been vaccinated.

In accordance with this discovery, it is an object of the invention to provide the 20 kd *B. abortus* CuZnSOD and specific regions thereof useful in the construction of diagnostic reagents.

Another object of the invention is to provide diagnostic reagents for distinguishing between animals which have serum antibody of a natural *B. abortus* infection and those which have an antibody response to a *B. abortus* Strain 19 vaccine or a mutant *B. abortus* Strain which does not express the 20 kd protein.

Other objects and advantages of the invention will become readily apparent from the ensuing description.

Deposit of Biological Material

An *E. coli* clone transformed with the plasmid pBR325(BACuZnSOD) has been deposited under the conditions of the Budapest Treaty with the Agricultural Research Service Culture Collection in Peoria, IL. The deposited culture was identified as *E. coli* 71-18 Strain pBA20-15-9 coding for the *B. abortus* CuZnSOD and has been assigned Accession No. NRRL B-18752.

BRIEF DESCRIPTION OF THE DRAWING

FIG. 1 shows the digestion product peptide components of the 20 kd *B. abortus* CuZnSOD protein.

FIG. 2 is an IgG ELISA with recombinant *B. abortus* CuZnSOD protein using sera from field-infected cattle.

FIG. 3 is a graph of the competitive inhibition data of anti-SOD by the peptide diagnostic reagent represented by SEQ ID NO. 2.

FIG. 4 is bar graph illustrating comparison of conventional serologic results to SOD-ELISA described in Example 7.

DETAILED DESCRIPTION OF THE INVENTION

The 20 kd *B. abortus* CuZnSOD protein useful as a diagnostic reagent within the scope of this invention may be isolated from *B. abortus* Strain 19 by any conventional procedure, such as column chomatography, as described in Tabatabai et al. [*Vet. Microbiol.* 20: 49–58 (1989)], herein incorporated by reference, and as described in Example 1, below. Alternatively, the equivalent, recombinant form of the protein may be expressed and isolated from *E. coli* 71-18 Strain pBA20-15-9, [Bricker et al., *Infect. Immun.*, 58: 2935–2939 (1990)] deposited in the NRRL culture collection and assigned Accession No. NRRL B-18752. The protein could, of course, also be synthesized from the amino acid sequence information given in SEQ ID NO. 1. Though the protein has an apparent molecular weight of approximately 20,000 daltons by SDS electrophoresis under denaturing conditions, its molecular weight based upon the 154 amino acid sequence is 16,071 daltons. For purposes of convenience, the protein will hereafter be referred to as the 20 kd protein or the CuZnSOD protein of *B. abortus*. This protein is further characterized by having an isoelectric point of 8.6.

The region of SEQ ID NO. 1 which has been characterized as the amphipathic helix of the CuZnSOD protein extends from Amino Acid 137 to Amino Acid 142. Peptide diagnostic reagents encompassing the helix and having the property of binding to T-cell receptors in an immune response could include flanking segments on either side of the region. One such peptide reagent which has been constructed as described in Example 3, below consists of Amino Acids 130 through 143. This peptide is presented in the Sequence Listing as SEQ ID NO. 2.

Other regions of the protein comprising antigenic determinants include Amino Acids 9 through 21, 58 through 63, and 121 through 126 in SEQ ID NO. 1. It is envisioned that peptide diagnostic reagents encompassing these regions could be readily constructed in same manner as the peptide corresponding to SEQ ID NO 2, discussed above. These peptides may be synthesized by known methods from the amino acid sequence information given in the sequence listing. They can also be expressed by synthetic genes. It is envisioned that the reagents constructed around the identified antigenic regions would encompass at least about 12 amino acids. Preferably the peptide reagents would have a length of 12–14 amino acids for optimal specificity.

The CuZnSOD protein and its antigenic peptide determinants can be used in an indirect enzyme immunoassay wherein the CuZnSOD protein or the antigenic peptide determinants are bound to the microtiter plate by adsorption. Antibody to the CuZnSOD protein or to the antigenic peptide determinants present in the serum of *B. abortus*-infected host animal binds to the antigen(s) adsorbed onto the plate. A second antibody (anti-host IgG) labeled with horseradish peroxidase or the equivalent is then incubated with the host antibody-antigen complex. Bound secondary antibody is detected by addition of a chromogenic substrate solution for the horseradish peroxidase, and the resulting colored solution is measured spectrophotometrically or colorimetrically. The intensity of the resulting absorption is proportional to the amount of anti-CuZnSOD or anti-antigenic peptide antibody.

In the competitive enzyme immunoassay, the CuZnSOD protein antigen is bound to the microtiter plate and several serial dilutions of the test and control sera are incubated with various increasing concentrations of the antigenic peptide determinant. Residual antibody (antibody not bound to the peptide) is then detected using the indirect ELISA as described above. In the competitive enzyme assay the intensity of absorption is inversely proportional to anti-CuZnSOD protein antibody in the serum of infected animals. A third application is to bind the antigen to nitrocellulose membranes or any solid phase designed to bind proteins or peptides by applying an aliquot of an appropriate concentration of the CuZnSOD or antigenic peptide determinant in a buffer such as 5 mM $NH_4HCO_3$. Either gridded nitrocellulose, various slotted apparati containing nitrocellulose, or "dipsticks" containing nitrocellulose can be used. After addition of the antigen, the nitrocellulose is blocked, such as with 3% fish gelatin; and either a single dilution or serial dilutions of test and control sera are then added or applied, and the membranes are incubated. After this step, the membranes are washed and incubated with a secondary antibody prepared against the host IgG, which is labeled with horseradish peroxidase or the equivalent. The enzyme reaction is detected using an insoluble chromogen-hydrogen peroxide substrate solution. The intensity of the color is proportional to the anti-CuZnSOD antibody in the serum.

Instead of using an enzyme-labeled antibody, other "reporter" groups can be used. These include radioisotopes ($^{125}I$), fluorescent probes, or streptavidin-biotin-labeled secondary antibodies. All these are generally available.

The invention is further illustrated by the following examples.

EXAMPLE 1

Isolation of Protein

*E. coli* 71-18 Strain pBA20-15-9 cells containing the recombinant gene for *B. abortus* CuZnSOD protein were grown in autoclaved LB medium, supplemented with 50 μg/ml of ampicillin. Washed *E. coli* cells were suspended in 1M sodium chloride-0.1M sodium citrate, pH 7.9. The suspension was extracted by gentle stirring overnight at 5° C. and centrifuged at 12,000 ×g for 20 min. The pelleted solids were reextracted with 1.0M sodium chloride-0.1M sodium citrate by gentle stirring overnight at 5° C., and the suspension was centrifuged at 12,000 ×g for 20 min. The resultant protein-containing supernatants were combined and dialyzed against 5 mM ammonium bicarbonate until the dialysis solution tested negative for chloride ion. The protein solution was then concentrated by lyophilization, and resuspended in a small volume of 5 mM ammonium bicarbonate. Solid ammonium sulfate (0.472 g/ml of protein solution) was then added slowly to the protein solution while stirring constantly at room temperature. When all the ammonium sulfate was dissolved, the solution was placed at 5° C. for 16 hr. The precipitated protein was removed by centrifugation (20,000 ×g), dialysed, lyophilyzed and stored at −70° C. The supernatant solution was measured and solid ammonium sulfate (0.237 g/ml of protein solution) was added slowly while stirring constantly at room temperature. When the ammonium sulfate was dissolved, the protein solution was stored at 5° C. for 16 hr. The solution was centrifuged at 20,000 ×g and the precipitated protein redissolved in a small amount of 5 mM ammonium bicarbonate and dialyzed until the dialysis solution was negative for sulfate ion (the supernatant was saved, dialyzed as described, lyophilized and stored at −70° C.). The protein concentration was determined as previously described (Tabatabai et al., 1979, supra). Two hundred microliters of protein solution was applied to an anion exchange column ("AX-300", Synchrom, Inc., Lafayette, Indiana) and equilibrated with 10 mM sodium phosphate buffer, pH 6.8. The protein was eluted with a linear gradient of 0 to 0.5M sodium chloride in 10 mM sodium phosphate buffer, pH 6.8. Protein elution was monitored by absorption at 214 nm rather than at 280 nm, as the protein does not absorb at 280 nm. Fractions were recovered containing protein with a molecular weight of 20 kd as measured by denaturing SDS gel electrophoresis and having antibody reactivity using a dot blot enzyme-immunoassay using rabbit antibody prepared to the recombinant protein and horseradish peroxidase-labelled goat-anti-rabbit serum. The fractions were combined, lyophilized, redissolved in a small mount of 5 mM ammonium bicarbonate and dialyzed until the dialysis solution was free of phosphate.

EXAMPLE 2

Amino Acid Sequencing

The amino acid sequencing of the B. abortus CuZn-SOD protein was conducted on a recombinant form of the protein. The lyophilized recombinant protein purified by anion-exchange chromatography was precipitated with methanol-chloroform-water to remove salts. Cysteine residues were modified with 4-vinylpyridine in preparation for chemical or enzymatic digestion. The protein (500 μg) was solubilized in 200 μL of 0.01% $NH_4HCO_3$ in the presence of 6M urea. The sample was preincubated at 25° C. for 30 min in the presence of 140 mM 2-mercaptoethanol (2 μL) before modification with 270 mM 4-vinylpyridine (6 μL) for 90 min at 25° C. The amino acid sequence of the recombinant protein was determined by automated Edman degradation of peptides originating from cleavage of the protein at methionine by CNBr, at arginine by clostripain (Sigma) digestion, and at glutamic acid by *Staphylococcus aureus* protease V8 (Sigma) digestion. The CNBr cleavage was performed by dissolving the pyridylethylated protein (500 μg) in 70% formic acid and adding an equal volume of 80 mg of CNBr/mL in 70% formic acid. The reaction was allowed to proceed in the dark at 25° C. for 20 hr. Clostripain digestion was performed by activating clostripain in 5 mM DTT and 1.5 mM $CaCl_2$ for 3 hrs. at 25° C. The pyridylethylated protein (500 μg) was solubilized in 30 mM $NH_4HCO_3$, 5 mM DTT, 2 mM CaCl2, and 6M urea. Clostripain was added at a weight ratio of 100:1 (protein:clostripain ratio), and the protein was digested overnight at 37° C. The *S. aureus* protease digestion was performed by dissolving the protease in 50 mM $NH_4HCO_3$ and 2 mM EDTA. The pyridylethylated protein (500 μg) was solubilized in 50 mM $NH_4HCO_3$ and 6M urea. The *S. aureus* protease was added at a weight ratio of 30:1 (protein:protease ratio), and the protein was digested for 4 hr at 37° C. Peptides were separated by reverse-phase HPLC on a Waters chromatography system using a 5-μm Vydac C-18 column (0.46×25 cm) and a linear gradient of 0.1% trifluoroacetic acid (solvent A)/90% acetonitrile (solvent B). Automated Edman degradation was performed on an Applied Biosystems Model 470-A gas-phase sequencer equipped with an on-line microbore HPLC system (Model 120-A) for phenylthiohydantion-derivatized amino acid identification. The protein was hydrolyzed for 1 hr at 150° C. using the gas-phase procedure of Bidlingmeyer et al. [*J. Chromatogr.* 336: 93–104 (1984)]. The samples were derivatized after dilution with 250 ppm of EDTA with an Applied Biosystems Model 420A derivatizer equipped with an on-line Applied Biosystems Model 130A HPLC system and a Model 920A data system.

The first 50 amino acids were determined by N-terminal sequence analysis of the protein as shown in FIG. 1. Five peptides were generated from CNBr digestion (CB1, CB2, CB3, CB4, and CB5). CB1 and CB2 were aligned by using the amino acid sequence already known from N-terminal sequence analysis. CB3 was completely sequenced and its order determined by overlapping with the clostripain-digested peptides. CB4 was partially sequenced to residue 122 and CB5 to residue 154. Clostripain digestion resulted in four peptides (CL1, CL2, CL3, and CL4). CL1 was partially sequenced to residue 42, and CB3 was aligned from this sequence. CL2 was sequenced to residue 122, and CB4 was aligned from this sequence. CL3 and CL4 were completely sequenced, and CB5 was aligned from these two fragments. *Staphyloccoccus aureus* V8 protease digestion allowed determination of two peptides (SA10 and SA11) at the carboxyl-terminal end of the protein. These two peptides provided information for overlap regions that could not be verified from sequence information obtained from the other peptides.

On the basis of amino acid sequence data, the molecular weight of the Brucella protein was 16,071. The amino acid chain length for the Brucella protein was 154 amino acids.

The complete amino acid sequence of the recombinant *B. abortus* CuZnSOD protein is given below in the Sequence Listing as SEQ ID NO. 1.

EXAMPLE 3

Identification of Antigenic Determinant

The protein isolated by the procedure of Example 1 was analyzed by the computer program "Antigen" ("PCGene" Software, Intelligenetics) to asertain regions of antigenicity. The following regions were identified:

| Region | Amino Acids |
|---|---|
| 1 | 9-21 |
| 2 | 58-63 |
| 3 | 121-126 |
| 4 | 137-142 (amphipathic helix). |

Synthesis of Peptide Comprising Region 4 (SEQ. ID NO. 2)

The peptide was synthesized on an Applied Biosystems Model 430A peptide synthesizer (0.5 mM scale) using p-methylbenzyl hydrylamine polystyrene resin and tert-butyloxycarbonyl (Boc)-protected amino acids (Applied Biosystems) Boc-Gly, Boc-Leu, Boc-Pro, Boc-Glu (O-benzyl), Boc-Lys (2-chlorobenzyloxycarbonyl), Boc-Asp (O-benzyl), Boc-Ser (O-benzyl), Boc-Tyr (2-bromobenzyloxycarbonyl), Boc-Asn, Boc-Gly. The protected peptide was deprotected and cleaved from the resin by treatment with anhydrous hydrogen fluoride using an apparatus designed by Amino Dynamics. The cleaved product was extracted with ether, followed by acetic acid and lyophilized. The lyophilized product was redissolved in a small amount of distilled water and again lyophilized, and the peptide was stored at room temperature. The sequence of the peptide was confirmed by amino acid sequencing using a Model 470A Applied Biosystems sequencer as described in Example 2.

EXAMPLE 4

IgG ELISA with Recombinant B. abortus CuZnSOD Protein Bovine Sera

Bovine sera were selected to provide a spectrum of reactions that might be encountered under field conditions. A positive control serum was collected from an experimentally infected cow at necropsy 4 mo after abortion (cow 47 was experimentally infected with $4 \times 10^7$ B. abortus Strain 2308). A negative control serum was a composite of 73 pooled sera of unvaccinated brucellosis-free cattle. Sera were used from calves vaccinated with $3 \times 10^9$ Strain 19 collected at 3 wks post-vaccination; sera from sexually mature cows experimentally infected with $3 \times 10^7$ B. abortus Strain 2308 and collected at 4 mo, post-exposure; and sera from naturally and experimentally infected cattle were obtained from the serum bank located at the National Veterinary Services Laboratory, Science and Technology, APHIS.

ELISA

The ELISA used was essentially that of Tabatabai et al. [J. Clin. Microbiol. (1984), supra], except that a blocking step with 3% fish gelatin was employed after the microtiter plates were coated with antigen.

Solid-phase antigens were diluted to 2.0 mg of protein per ml in 5 mM NH$_4$HCO$_3$ and stored frozen in 10-μL samples). Microtiter plates (Immulon 1: Dynatech Laboratories, Alexandria, VA) were coated with 100 μL of 0.5M NaCO$_3$, pH 9.6, containing antigens at 0.2 μg/ml of CuZnSOD protein or 100 μg/ml of peptide (SEQ. ID NO. 2) and stored overnight at 5° C. Plates were washed five times for 5 min with 200 μL of saline-0.05% Tween 80 (Difco Laboratories, Detroit, MI) and blotted between washes. Plates were incubated 15 min at room temperature with PBS-Tween containing 3% fish gelatin (Norland Products, Inc., New Brunswick, NJ). Test and control sera were diluted 1:100 or serially, as designated, in 50 mM phosphate-buffered saline (pH 7.2)-0.05% Tween 80 (PBS-Tween), dispensed in plates in 100-μL quantities and incubated for 2 hr at room temperature. The washing procedure was repeated and horseradish peroxidase-conjugated goat antibovine IgG (Cappell Organon Teknika, Westchester, PA; heavy chain specific) was diluted 1:1000 in PBS-Tween. Plates were incubated for 2 hr at room temperature or overnight at 5° C. The washing procedure was repeated, and the enzyme reaction was initiated by adding 100 μL of substrate solution containing 5 mM H$_2$O$_2$ (0.015%) and 0.2 mM ABTS (2,2'-azino-di-(3-ethyl-benzthiazoline-6-sulfonic acid)] (Sigma Chemical Co., St. Louis, MO) in 50 mM sodium citrate (pH 4.0). After exactly 10 min of incubation at room temperature, the reaction was stopped by the addition of 100 μL of 0.1M hydrofluoric acid (the enzyme reaction was linear with time for 15 min). The absorbance ratio at 410 nm/450 nm (to minimize plate to plate differences) was recorded with a "Model 600" plate reader (Dynatech Laboratories). The results are illustrated in FIG. 2.

Results of ELISA with the CuZnSOD Protein

Figure 2:
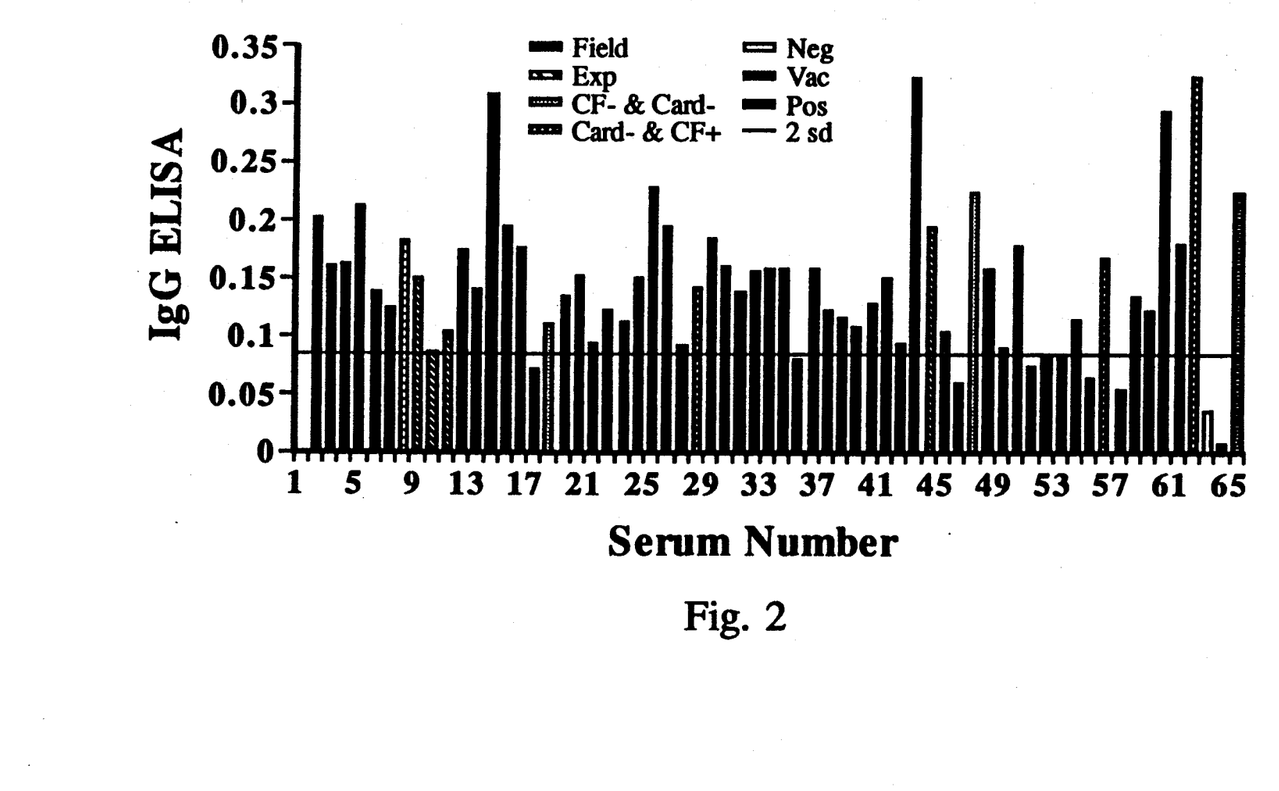

FIG. 2 is a bar graph showing data from naturally-infected (Field), a first set of experimentally infected [(Exp) totalling 61 sera], a second set of experimentally infected [(Pos); 10 sera], Brucella-free [(Neg); 10 sera] and from calfhood-vaccinated [(Vac); 10 sera] animals. The sera obtained from APHIS are identified in FIG. 2 as "Field", "Exp", CF-negative and Card-negative ("CF- & Card-"), or Card negative and CF positive ("Card- & CF+").

The bar graph demonstrates the results of each of the APHIS sera (61 total) and those with the negative, positive, and calfhood vaccinated animals. The horizontal line indicates the mean of the "negative" group plus 3 standard deviations.

Results of ELISA with the Peptide

In regard to the peptide ELISA, sera from 12 naturally-infected animals obtained from APHIS and positive and negative control sera were tested with the peptide ELISA. All sera from the naturally-infected animals and the positive control serum showed ELISA results approximately 2-fold greater than the mean of the negative control sera plus 3 standard deviations.

EXAMPLE 5

Competitive ELISA with Antigenic Peptide Determinant

A positive serum was collected from a rabbit immunized with the CuZnSOD protein isolated from recombinant E. coli expressing the B. abortus Strain 19 CuZnSOD protein. Antiserum to recombinant B. abortus CuZnSOD protein was obtained from New Zealand White rabbits injected initially with 1 ml intradermally (multiple injection sites). The inoculum contained 50 μg of protein per ml and was incorporated in Freund's complete adjuvant. Three subsequent intramuscular injections, 1 ml each, were given at weekly intervals. Rabbits were anesthetized and exsanguinated 1 wk following the last injection. Sera were stored at −70° C. until used [Tabatabai et al., Vet. Microbiol. (1984), supra].

Figure 3:
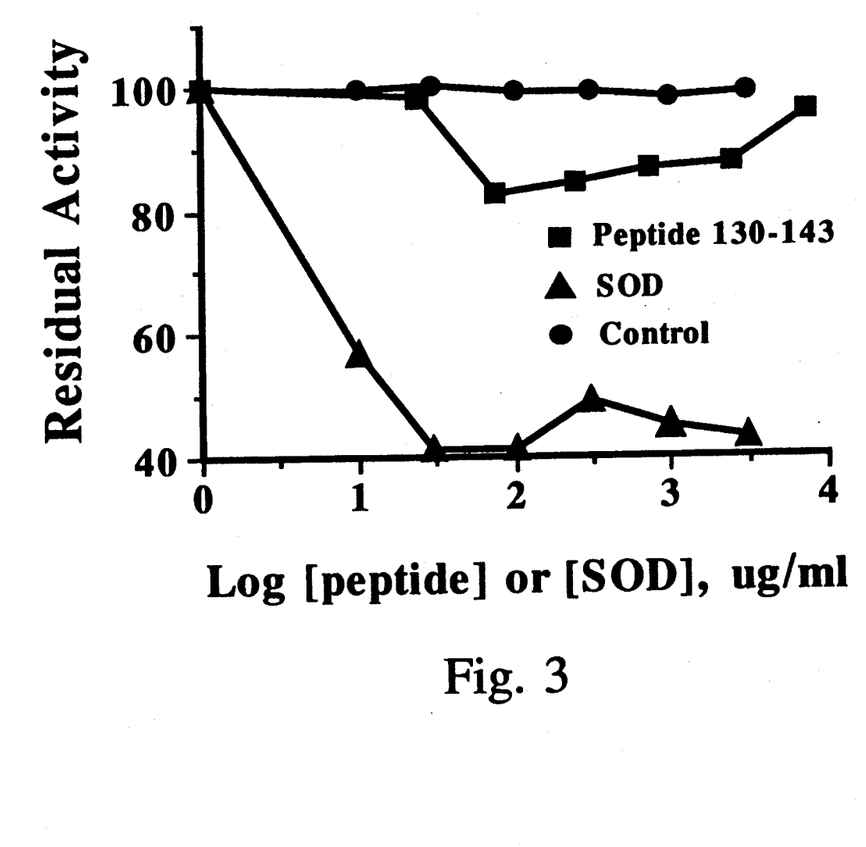

The competitive ELISA used was essentially that of Nielsen et al., [Ann. Inst. Pasteur, Microbiol., supra], except that we employed CuZnSOD protein as the solid-phase antigen and polyclonal antibodies to the CuZnSOD protein and the peptide (SEQ ID NO. 2). The CuZnSOD protein antigen was diluted to 2 μg/ml in 5 mM NH$_4$HCO$_3$ and stored frozen in 20-μL samples. Microtiter plates (Immulon 1: Dynatech Laboratories, Alexandria, VA) were coated with 200 μL of 0.5M NaCO$_3$, pH 9.6, containing antigen at 2 μg/ml. Plates were washed 5X for 5 min with 200 μL of saline-0.5% Tween 80 (Difco Laboratories, Detroit, MI) and blotted between washes. The microtiter plates were then blocked with 3% fish gelatin (Norland Products, Inc., New Brunswick, NJ) in 50 mM phosphate-buffered saline (pH 7.2)-0.05% Tween 80 (PBS-Tween 80) for 15 min at room temperature. The blocking solution was removed from the microtiter plate by shaking it dry, and the plate was blotted. Test and control rabbit and mouse sera were diluted at 1:10, 1:50, and 1:100 in PBS-Tween 80 and 100 μL of each dilution of serum was incubated with various concentrations of the antigenic peptide for 1 hr at room temperature. The antibody-peptide mixture was added to the wells of the microtiter plate and incubated for 1 hr at room temperature. The washing procedure was repeated and horseradish peroxidase-conjugated goat-antirabbit IgG (heavy chain specific) or horseradish peroxidase goat antimouse IgG (heavy chain specific) (both from Appel, Organon Teknika, Westchester, PA) were diluted 1:2000 and 1:1000, respectively. Plates were incubated for 1 hr at room temperature or 16 hr at 5° C. The washing procedure was repeated, and the enzyme reaction was initiated by adding 100 μL of substrate solution containing 5 mM H$_2$O$_2$ (0.015%) and 0.2 mM ABTS (2,2'-azino-di[3-ethyl-benathiazolinone-6-sulfonic acid)] (Sigma Chemical Co., St. Louis, MO) in 50 mM sodium citrate (pH 4.0). After exactly 10 min of incubation at room temperature, the reaction was stopped by the addition of 100 μL of 0.1M hydrofluoric acid (the enzyme reaction was linear with time for 15 min). The absorbance ratio at 410 nm/450 nm (to minimize plate to plate differences) was recorded with a "Model 600" plate reader (Dynatech Laboratories). The data are expressed in FIG. 3 as percent inhibition compared to test and control serum dilutions without addition of peptide.

EXAMPLE 6

Western Blot of Bovine Serum with B. abortus CuZnSOD

To ascertain that the antibody to B. abortus detected by the CuZnSOD is specific to the CuZnSOD protein, Western blotting was employed, for the specific detection of the 20 kd protein band, which will be evident as a purple-blue band at 20 kd. The SDS gel containing the CuZnSOD protein (performed as described in Belzer et al., supra) is equilibrated from 30 min in blotting buffer which is composed of 25 mM Tris-base, 192 mM glycine, and 20% (v/v) of methanol [Towbin et al., Proc. Nat. Acad. Sci. 76: 4350-4354 (1979)]. Nitrocellulose membranes, BA-85, were from Schleicher and Schull (Keene, NH). Electrophoretic blotting was performed at 30 V and 0.11 A for 16 hr using a "Transblot" apparatus (Bio-Rad). Following electrophoretic transfer, the nitrocellulose sheets were rinsed twice in distilled water. The sheets were then incubated for 15 min with a solution containing phosphate buffered saline PBS-Tween 80 and 3% liquid fish gelatin (Norland Products, Inc., New Brunswick, NJ). The blocking solution was removed, and the bovine antisera described in Example 4 plus a serum bank (NVSL, APHIS) consisting of sera from naturally and experimentally infected animals diluted 1:500 with PBS-Tween in 0.2% (w/v) gelatin, or in 3% fish gelatin, was then added to nitrocellulose membranes and incubated for 2 hr at room temperature. The membranes were washed five times for 5 min each time with PBS-Tween and subsequently placed in horseradish peroxidase-labeled antibovine IgG conjugate (heavy chain-specific) (Cappel, Orgahon Teknika, West Chester, PA), diluted 1:500 in PBS-Tween-gelatin, and incubated for 2 hr at room temperature. The membrane was washed as described above, the substrate solution was added, and the membrane incubated until bands were sufficiently developed. The substrate solution was composed of 0.3% (w/v) 4-chloronaphthol (Sigma, St. Louis, MO) and 0.01% H$_2$O$_2$ in 0.1M PBS, pH 7.2. One portion of the nitrocellulose membrane containing an identical protein blot was stained for 2 min with an Amido Black solution (K&K Laboratories, Inc., Jamaica, NY) consisting of 0.1% (w/v) Amido Black, 25% (v/v) isopropanol, and 10% acetic acid, and destained with a solution containing 25% (v/v) isopropanol and 10% (v/v) acetic acid.

EXAMPLE 7

Comparison of SOD-ELISA to other serologic tests

The recombinant B. abortus CuZnSOD was employed as a diagnostic reagent in the indirect ELISA test described in Example 4 using a serum bank (NVSL, APHIS) consisting of sera from naturally and experimentally infected animals. The use of the recombinant B. abortus CuZnSOD protein for detecting infected animals was compared to the results obtained by using conventional serologic tests as described by Alton et al., supra, for the buffered B. abortus plate antigen (BAPA), Card, complement fixation (CF), standard plate test (SPT), rivanol precipitation test (RIV) and standard tube test (STT); and by Huber et al., [Proc. USAHA (1989)] for the particle concentration fluorescence inhibition assay (PCFIA).

Figure 4:
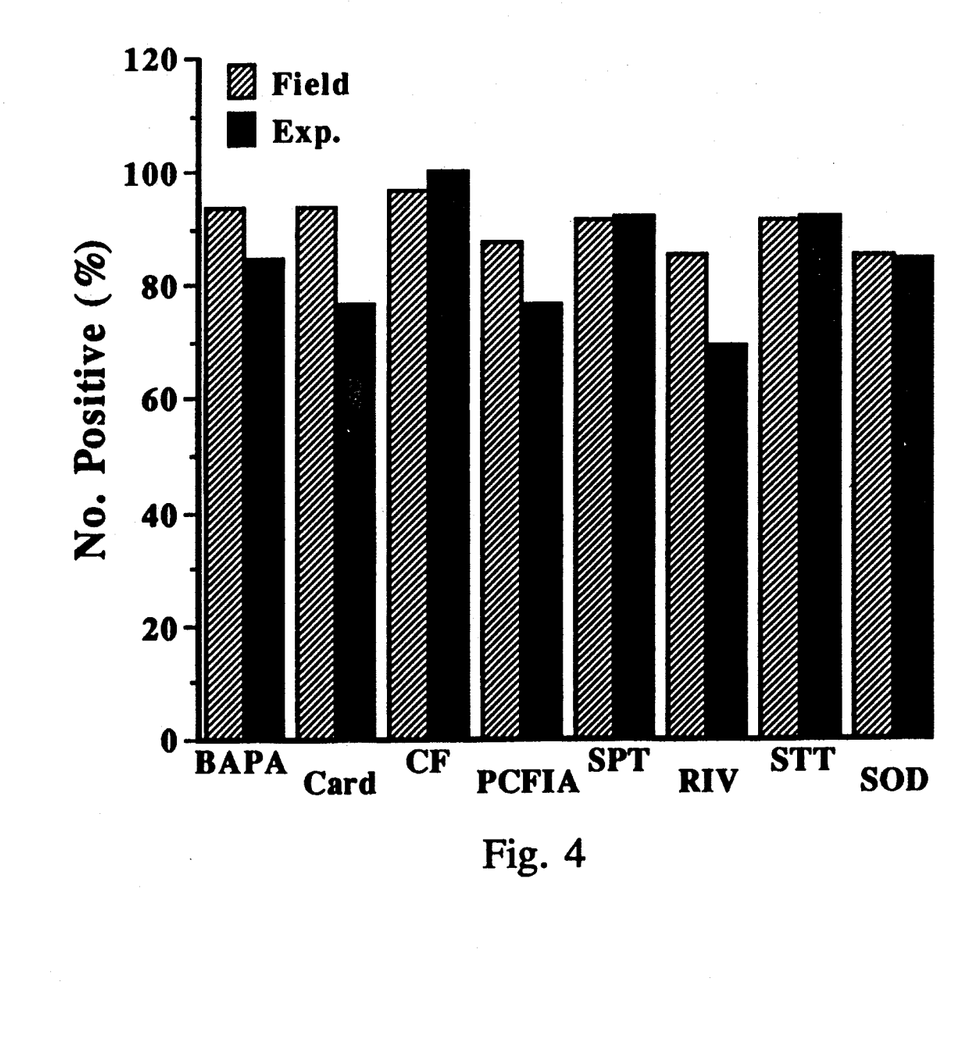

As shown in FIG. 4, the CuZnSOD protein detects B. abortus-infected animals equally well as the PCFIA and RIV tests. Even though the agglutination tests (BAPA, Card, SPT, STT) detect a higher percentage of animals, these tests cannot always distinguish titers due to vaccination from infection. The CF test is sensitive and specific, but is cumbersome.

---

We claim:

1. A method of detecting an antibody elicited in response to the presence of B. abortus containing B. abortus copper-zinc superoxide dismutase protein, CuZnSOD protein, comprising the steps of combining a diagnostic reagent comprising a substantially pure B. abortus CuZnSOD protein or a segment of the B. abortus CuZnSOD protein effective as an antigenic determinant, with a body fluid sample suspected of containing said antibody and detecting the presence of a complex of said reagent and said antibody.

2. A method as described in claim 1 wherein said reagent comprises the substantially pure B. abortus CuZnSOD protein.

3. A method as described in claim 1 wherein said reagent comprises a segment of the B. abortus CuZnSOD protein effective as an antigenic determinant.

4. A method as described in claim 3 wherein said segment is a peptide having at least about 12 amino acids.

5. A method as described in claim 4 wherein said segment comprises the amino acid sequence of SEQ ID NO. 2.

6. A method as described in claim 1 wherein said reagent is labelled with a detectable moiety.

7. A method as described in claim 1 wherein said body fluid is bovine serum.

* * * * *

UNITED STATES PATENT AND TRADEMARK OFFICE
CERTIFICATE OF CORRECTION

PATENT NO. : 5,188,936

DATED : February 23, 1993

INVENTOR(S) : Louisa B. Tabatabai, John E. Mayfield, and Bonnie L. Beck

It is certified that error appears in the above-identified patent and that said Letters Patent is hereby corrected as shown below:

On title page, item [73], insert -- and Iowa State University Research Foundation, Inc., Ames, IA -- .

Signed and Sealed this

Fifth Day of July, 1994

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,188,936
DATED : February 23, 1993
INVENTOR(S) : Louisa B. Tabatabai, John E. Mayfield, and Bonnie L. Beck It is certified that error appears in the above-identified patent and that said Letters Patent is hereby corrected as shown below:

On Title Page, before [45] and at [75], delete "Tabatabi" and insert -- Tabatabai -- .

Signed and Sealed this

Sixteenth Day of May, 1995

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 2

( v i ) CURRENT APPLICATION DATA:
( A ) APPLICATION NUMBER: Serial No. 07/641,346

(B) FILING DATE: January 16, 1991

(2) INFORMATION FOR SEQ ID NO:1:

(i) SEQUENCE CHARACTERISTICS:

(A) LENGTH: 154

(B) TYPE: amino acid

(D) TOPOLOGY: linear

(ii) MOLECULE TYPE: protein

(xi) SEQUENCE DESCRIPTION: SEQ ID NO:1:

```
Glu Ser Thr Thr Val Lys Met Tyr Glu Ala
 1               5                    10
Leu Pro Thr Gly Pro Gly Lys Glu Val Gly
                15                    20
Thr Val Val Ile Ser Glu Ala Pro Gly Gly
                25                    30
Leu His Phe Lys Val Asn Met Glu Lys Leu
                35                    40
Thr Pro Gly Tyr His Gly Phe His Val His
                45                    50
Glu Asn Pro Ser Cys Ala Pro Gly Glu Lys
                55                    60
Asp Gly Lys Ile Val Pro Ala Leu Ala Ala
                65                    70
Gly Gly His Tyr Asp Pro Gly Asn Thr His
                75                    80
His His Leu Gly Pro Glu Gly Asp Gly His
                85                    90
Met Gly Asp Leu Pro Arg Leu Ser Ala Asn
                95                   100
Ala Asp Gly Lys Val Ser Glu Thr Val Val
               105                   110
Ala Pro His Leu Lys Lys Leu Ala Glu Ile
               115                   120
Lys Gln Arg Ser Leu Met Val His Val Gly
               125                   130
Gly Asp Asn Tyr Ser Asp Lys Pro Glu Pro
               135                   140
Leu Gly Gly Gly Gly Ala Arg Phe Ala Cys
               145                   150
Gly Val Ile Glu
```

(2) INFORMATION FOR SEQ ID NO:2:

(i) SEQUENCE CHARACTERISTICS:

(A) LENGTH: 14

(B) TYPE: amino acid

(D) TOPOLOGY: linear

(ii) MOLECULE TYPE: protein

(xi) SEQUENCE DESCRIPTION: SEQ ID NO:2:

-continued

```
Gly  Gly  Asp  Asn  Tyr  Ser  Asp  Lys  Pro  Glu
 1              5                           10
Pro  Leu  Gly  Gly
```